(12) United States Patent
Vollmer

(10) Patent No.: US 9,320,721 B2
(45) Date of Patent: Apr. 26, 2016

(54) MUCOADHESIVE PATCH WITH OPPOSITE RATIOS OF NONIONIC AND ANIONIC HYDROCOLLOIDS IN ADHESIVE AND BACKING LAYER

(75) Inventor: Ulrike Vollmer, Dormagen (DE)

(73) Assignee: TESA LABTEC GMBH, Langenfeld (DE)

( * ) Notice: Subject to any disclaimer, the term of this patent is extended or adjusted under 35 U.S.C. 154(b) by 2365 days.

(21) Appl. No.: 11/661,712

(22) PCT Filed: Sep. 1, 2005

(86) PCT No.: PCT/DE2005/001528
§ 371 (c)(1),
(2), (4) Date: Oct. 1, 2007

(87) PCT Pub. No.: WO2006/024284
PCT Pub. Date: Mar. 9, 2006

(65) Prior Publication Data
US 2008/0274164 A1 Nov. 6, 2008

(30) Foreign Application Priority Data
Sep. 1, 2004 (DE) .......................... 10 2004 042 616

(51) Int. Cl.
*A61K 9/70* (2006.01)
*A61K 9/00* (2006.01)

(52) U.S. Cl.
CPC ............... *A61K 9/7084* (2013.01); *A61K 9/006* (2013.01); *A61K 9/0034* (2013.01); *A61K 9/7007* (2013.01)

(58) Field of Classification Search
None
See application file for complete search history.

(56) References Cited

U.S. PATENT DOCUMENTS

| 3,699,963 A | 10/1972 | Zaffaroni | |
|---|---|---|---|
| 5,166,233 A * | 11/1992 | Kuroya et al. | 524/37 |
| 2002/0142036 A1* | 10/2002 | Rupprecht et al. | 424/484 |
| 2006/0039957 A1* | 2/2006 | Krumme | 424/443 |
| 2006/0228427 A1* | 10/2006 | Levine et al. | 424/725 |

FOREIGN PATENT DOCUMENTS

| DE | 198 32 519 A1 | 1/2000 | |
|---|---|---|---|
| EP | 0 381 193 | 8/1990 | |
| EP | 0947350 A1 * | 10/1999 | B41M 5/00 |
| EP | 1 034 780 | 9/2000 | |
| WO | 0041670 A2 | 7/2000 | |
| WO | 00/59423 | 10/2000 | |
| WO | 01/30288 | 5/2001 | |
| WO | WO 2004/043426 * | 5/2004 | A61K 9/00 |
| WO | 2006024284 A2 | 3/2006 | |

\* cited by examiner

*Primary Examiner* — Kevin S Orwig
(74) *Attorney, Agent, or Firm* — Lucas & Mercanti, LLP; Klaus P. Stoffel

(57) ABSTRACT

A mucoadhesive patch that consists of an adhesive layer and a backing layer, wherein the adhesive layer contains a nonionic and an anionic hydrocolloid in a weight ratio of 1:2 to 1:5, and the backing layer contains a matrix of a nonionic and an anionic hydrocolloid in a weight ratio of 2:1 to 5:1.

12 Claims, No Drawings

MUCOADHESIVE PATCH WITH OPPOSITE RATIOS OF NONIONIC AND ANIONIC HYDROCOLLOIDS IN ADHESIVE AND BACKING LAYER

The invention concerns an atrium patch, also known as a buccal patch or mucoadhesive patch or Orasan.

The oral cavity, which has a surface area of about 100 cm$^2$, has an especially wide variety of functions in the human organism. It has the primary function of food intake, but it is also an organ which, on the one hand, must separate itself from the outside environment and, on the other hand, is already one of the internal organs. This is reflected in the various epidermal regions. Laterally, there is the buccal mucosa (called the buccal application side), above, there is the palate (called the palatal application site), and below, there is the space under the tongue (called the sublingual application site). In addition, the oral cavity contains the tongue (not an application site so far; important role in speech articulation). The mouth also contains the chewing tools (teeth) necessary for digestion. They are anchored in the gums (also known as the gingival application site). Foods introduced from the outside contain both high microbial loads and ideal nutrient conditions for these microorganisms with respect to nutrient sources, moisture, and temperature. Oral cavities with a high microbial load are characterized by painful inflammations, missing or decaying teeth, bad breath, and impaired absorption of food. To eliminate these problems, the industry offers numerous mouth care products, which include not only instruments, such as tooth brushes, dental floss, oral irrigators, etc., but also aids, such as toothpastes, mouthwashes, chewing gums, and systemic drugs (e.g., antibiotics). All of these aids can be used either by the patient himself or by professionals, such as dentists.

The specified application sides in the oral cavity are all distinguished by the presence of water, i.e., when a patch is applied, the adhesion must come about in a state of wetness/moisture. In this case, one also speaks of mucoadhesion, because the patch adheres to the mucous membrane, which is covered with mucous secretions. In this regard, mucoadhesion is viewed as a special type of bioadhesion, since any type of adhesion with at least one living phase is considered bioadhesion. The thickness of the buccal mucosa, which is not keratinized, is about 500-800 µm, while the mucous membranes of the hard palate, which is keratinized, and the mucous membranes of the gums are about 100-200 µm thick. The permeability of the oral mucous membranes is greater than that of the epidermis of the skin but less than that of the gastrointestinal tract. The special form of sublingual application is of no further interest here, since it is already very well studied but is suitable for only a small number of applications. The thinness of the mucosa and the good circulation promote rapid absorption and good bioavailability. The situation is different with gingival and buccal application. In the case of gingival application, permeability is poor and circulation is moderate, but the patch can be left in place for a long time. In the case of buccal application, the permeability is somewhat greater, circulation is good, and the patch can be left in place for a long time. Both sites of application are suitable for the application of patches that are intended to develop a local effect in the oral cavity. This is necessary, for example, in the case of oral diseases. Patches of this type can be used, for example, to apply disinfectants, antibiotics, antimycotics, virostatics, corticoids, etc., in some cases in the form of plant extracts, which arise in infections caused by bacteria, fungi and viruses, such as stomatitis, herpes, aphthae, or after tooth extractions. In addition, there is the need to prevent infections of lesions and ulcers, which, for example, occur with increased frequency in immunosuppressed persons. There is also a need for the application of local anesthetics for painful inflammatory processes or prosthetic pressure points. It is also possible to deliver flavorings, natural substances, or salts for the purpose of improving mouth odor or reducing the formation of plaque as a precursor of gingivitis and periodontitis.

There are other parts of the body with requirements very similar to those of the oral cavity, specifically, various body openings (orifices, cavities), such as the nose, the vagina, and the anus, as well as the skin surrounding them, such as lips, genitals, etc. At all of these body openings, the inside and outside of the organism communicate with the environment in the form of an exchange of substances, and consequently, these parts of the body have a mucosal lining of the epidermis and a need for organ-specific therapy with mucoadhesive systems.

A common feature of all mucoadhesive systems, such as the mucoadhesive patch cited here, is that they contain, on the side that is attached to the mucous membrane, adjuvant substances that are able to develop adhesion in this environment. Materials of this type are mentioned, for example, in the publication: J. D. Smart et al., J. Pharm. Pharmacol. Vol. 36, pp. 295-299, 1984. All of these substances are viscosity-increasing polymers, which may be of natural origin, e.g., gelatin, pectin, tragacanth, gum arabic, chitosan, hyaluronic acid, alginates, agar, etc., or semisynthetic, e.g., cellulose derivatives, including cellulose ethers, or fully synthetic polymers, e.g., polyacrylic acid derivatives with various degrees of crosslinking, polyvinyl alcohols, and polyvinyl pyrrolidones. These substances must be selected on the basis of various criteria. For one thing, the substances used to produce a patch must be capable of forming a film. For another, microbiological purity, mucosal compatibility, and compatibility with the active substances and adjuvants must be ensured.

When a mucoadhesive system is applied, the other side must be covered with a nonmucoadhesive layer to prevent the orifice from being bonded together (inflation). This results in several possibilities for designing the mucoadhesive patch: a local system delivers the active substance from the mucoadhesive layer directly to the mucous membrane to which it adheres, or a local system delivers the active substance from the nonmucoadhesive layer directly to the oral cavity. A systemic system, on the other hand, delivers the active substance from the mucoadhesive layer directly to the mucous membrane to which it adheres, and the active substance then enters the blood circulation, in which it develops central activity. In the discussion which follows, we will focus our attention more on the local systems, but not exclusively so.

Two-layer systems of this type have already been adequately described in the document DE 198 56 1001 A1.

For example, synthetic polyacrylic acid derivatives with the INCI name carbomer are used for the adhesive layer. The variably strongly crosslinked homopolymers carbomer 971 and 974 and carbomer 1342 (all from BF Goodrich) showed no great differences with respect to swelling and adhesion, and polycarbophil (BF Goodrich) can be used equivalently. The backing layer consisted of cellulose derivatives, such as hydroxypropyl cellulose (HPMC), which is also known by the trade name Pharmacoat (manufactured by Synthapharm), although HPMC alone exhibits hardly any mucoadhesiveness, and blending with cellulose derivatives (e.g., EP 275550 B1) usually reduces the adhesiveness of carbomers.

Surprisingly, it was then found that the joining of the two layers can be considerably improved by the addition of gum arabic. However, this polymer must be supplied to the rear layer, not the adhesive layer, because otherwise the system of the mucoadhesive patch is no longer possible.

Ethyl cellulose (Hercules, 48-49.5% ethoxyl content, degree of substitution 2.41-2.51, low viscosity) is used as a water-insoluble nonionic cellulose ether, and hydroxypropyl cellulose (Synthapharm, Pharmacoat 606, mol. wt. 11,000), i.e., a derivative comparable to the one used in the adhesive layer, is used as a water-soluble nonionic cellulose ether.

Carbopol 971 (BF Goodrich; carbomer 971 CP) is used as a water-insoluble anionic colloid, and the salt of arabic acid (gum arabic, produced by Caelo) is used as a water-soluble anionic colloid. The surprising discovery was made that the two layers are best joined by providing the water-insoluble anionic colloid with the water-soluble nonionic cellulose ether in the adhesive layer for the mucosa and providing the water-soluble anionic colloid with the water-insoluble cellulose ether in the backing layer. It is obvious to one skilled in the art that anionic and nonionic types of gums can be mixed but not anionic and cationic types. However, it was not obvious to one skilled in the art that the ratios of the anionic and nonionic hydrocolloids contained in the two layers must be related in an inverse way to obtain optimum adhesion to mucosal epidermal layers of body orifices.

Varying amounts of active substances in either dissolved or suspended form can be used. Active substances that can be used include, but are not limited to, the following: antiseptics, such as chlorhexidine, hexetidine, cetyl pyridinium, etc., antimycotics, such as miconazole, clotrimazole, econazole, nystatin, tolnaftate, sulbentine, itraconazole, etc., virostatics, such as amantadine, aciclovir, zidovudine, etc., antibiotics, such as tetracycline, metronidazole, clindamycin, etc., local anesthetics, such as tetracaine, benzocaine, lidocaine, etc., corticoids, such as triamcinolone, hydrocortisone, etc., salts of fluoride, potassium, zinc, etc., or vitamins, such as ascorbic acid, tocopherol, vitamin K, 8-carotene, coenzyme Q10, etc.

Aqueous or alcoholic extracts of plants, such as Echinacea, Sambucus, Matricaria, Thymus, Camiphora, Salix, Camelia, Salvia, Melissa, Myrtillum, Allium, etc., can also be used.

The patch must be produced in such a way that the adhesive layer and the active layer are inseparably joined. Since neither layer contains any binder whatsoever, and the lamination technology of conventional matrix patches is to be used, and thus no compression pressure is available, surprisingly, this joining could be achieved only by depositing the layers one above the other by overlayering. Due to the special ratios of the hydrocolloids that are selected and used, the use of phases of the same type (both aqueous or both organic) is no longer necessary. Nevertheless, the two layers do not mix, but they do become joined and are nonadhesive when dry, so that a siliconized protective foil, which is needed for other standard matrix patches, is not necessary during the production process or for packaging.

An ethanolic adhesive layer is first formed, for example, on polyester films, glass, or some other smooth surface. After it has dried, the active substance layer in an ethanolic suspension is applied as a coating above it. After complete drying has occurred, the system can be easily removed from the carrier substrate (polyester, glass, etc.). The sheet is then punched into individual doses of 0.5 to 2.5 cm², and preferably 0.8 to 1.25 cm², which are then packaged in peel packs that are impermeable to air and light, with which those skilled in the art are familiar.

The special feature of this invention is that the bond between the two layers is always especially good when the ratio of the hydrocolloids that are used is selected in such a way that nonionic polymers, such as hydroxypropylmethyl cellulose ether and ethyl cellulose ether, and anionic polymers, such as carbomer (polyacrylic acid as polyanion) and gum arabic (salt of arabic acid), are present in a ratio of 1:1 to 1:2, and preferably 1:1.2. On the other hand, it is important that the ratio of nonionic hydrocolloid to polyanionic hydrocolloid in the adhesive layer is 1:2 to 1:5, and preferably 1:3, but just the opposite in the backing layer, namely, 2:1 to 5:1, and preferably 3:1.

The specified hydrocolloids are merely specific examples. Naturally an expert is familiar with nonionic polymers other than those which have been cited here, such as cellulose ethers, for example, guar gum, carob bean flour, polyvinyl pyrrolidone, starch, etc., and anionic polymers other than those which have been cited here, such as carbomers and gum arabic, for example, agar, alginic acid, carboxymethyl cellulose, carrageenin, gelatin type B, karaya gum, pectin, tragacanth, polymethylvinyl ether/maleic anhydride (Gantrez), etc.

EXAMPLES

Example 1 in Accordance with the Invention

A patch laminate of the invention is produced on the laboratory scale with an area of 3,500 cm². The adhesive layer is produced as follows: 4.2 g of Pharmacoat 606 and 2.8 g of anhydrous glycerol are dissolved in 280 g of 96% ethanol, and then 0.42 g of titanium dioxide are homogeneously suspended in this solution. 14 g of carbomer 971 are sprinkled onto the ethanolic solution on a stirrer set to 300 rpm and 150° C. The system is then sealed and homogenized at room temperature for 60 minutes in a high-speed mixer. Slow stirring is then performed to remove the air that has worked itself into the solution. 1.4 g of strawberry flavoring (e.g., Dragoco) and 238.185 g of an aqueous plant extract from a dry extract of Sambucus nigra, Santella asiatica, Echinacea purpurea (9:0.8:0.2 wt., dry residue content 5.3%) are added. The solution is stirred, and a homogeneous, bubble-free and lump-free, brown gel is obtained, which is spread out on polyester (Hoechst, Hostaphan RN 100) with a wet layer thickness of 2,000 µm. The layer is dried for 30 minutes while the temperature is increased from 40° C. to 60° C. The backing layer is produced as follows: 18 g of ethyl cellulose are sprinkled onto 153 g of 96% ethanol, and the mixture is stirred at 700 rpm until the ethyl cellulose dissolves. 0.36 g of dye E172 red are dissolved in 2 mL of water. 0.45 g of titanium dioxide are ground in 9 g of castor oil, and 0.0.45 g are added while stirring. Finally, 6.75 g of gum arabic are added, and the whole mixture is stirred at 300 rpm until a homogeneous, light red, turbid, highly fluid suspension is obtained. The suspension is used to cover the adhesive layer with a wet layer thickness of 1,000 µm, which is likewise dried for 30 minutes while the temperature is increased from 40° C. to 60° C. Mucoadhesive patches with an area of 1.25 cm² and an elliptical shape are then punched out of the sheet. The patches each contain 4.5 mg of dry extract and are intended for the treatment of gingivitis and periodontitis.

The ratio of the nonionic to the anionic polymers in the present case is 1:1.2. The ratio within the adhesive layer is 1:3.3, and the ratio in the backing layer is 2.7:1.

Example 2 in Accordance with the Invention

A patch laminate of the invention is produced on the laboratory scale with an area of 2,000 cm². The adhesive layer is produced as follows: 3.1 g of Durotak 387-2353 (37.5% solids content), 3.85 g of Gantrez AN-139, and 3.5 g of aciclovir are dissolved in 17.7 g of 96% ethanol while stirring. 0.12 g of titanium dioxide are ground in 2 mL of 96% ethanol and 0.8 g of anhydrous glycerol, and 0.39 g of strawberry flavoring are added, and is homogenized. Slow stirring removes the air that has worked itself into the solution and a homogeneous, bubble-free and lump-free, white gel is obtained, which is spread out on polyester (Hoechst, Hostaphan RN 100) with a wet layer thickness of 2,000 µm. The layer is dried for 30 minutes while the temperature is increased from 40° C. to 60° C.

The backing layer is produced as follows: 6.154 g of ethyl cellulose are dissolved in 52.3 g of 96% ethanol, and 0.154 g of titanium dioxide are ground in 3 g of castor oil. The latter and 2.3 g of gum arabic are added to the ethanolic ethyl cellulose solution, which is then homogenized by stirring. Coloring and flavoring can also be added. The solution is applied over the adhesive layer with a wet layer thickness of 600 µm, which is then dried for 20 minutes at 50° C. Mucoadhesive patches with an area of 1.25 cm$^2$ and an elliptical shape are punched out of the sheet. The patches each contain 5 mg of aciclovir and are intended for the treatment of herpes labialis and herpes genitalis.

Example 3 in Accordance with the Invention

The patch produced as described in Example 3, but without the active ingredient, was tested in an internal company test in which it was worn by volunteer test subjects of both sexes for the purpose of determining its characteristics with respect to application, duration of adhesion, and general convenience. At the time of testing, none of the participants had a labial herpes lesion, and only one of eight participants is a herpes patient.

After a test patch was issued to a test subject, the results were evaluated on the basis of a multiple-choice questionnaire. The test was conducted over a period of one week. 77% found the patches easy to use. The patch is applied by moistening lips that are fat-free with the tongue and then pressing the white side of the patch against the moist lip for 30 seconds until the patch firmly adheres to the lip. 77% of the test subjects had the feeling of a foreign body being present on their lip. 62.5% of the participants judged the adhesion of the patch to be good and found the patch to be neutral in taste. The average length of time the patch was worn was 5.6 hours, the minimum time was 1.3 hours, and the maximum time was 19 hours. In each case the patch was actively removed by the test subject; it never fell off spontaneously. 50% of the participants thought that the patch could be improved by making it still thinner or more flexible and more neutral in color. These demands can be easily met by producing the backing layer by applying a thinner coating and by changing the dyes.

Example 4 in Accordance with the Invention

A patch laminate of the invention is produced on the laboratory scale with an area of 3,500 cm$^2$. The adhesive layer is produced as follows: 4.2 g of Pharmacoat 606 and 2.8 g of anhydrous glycerol are dissolved in 280 g of 96% ethanol, and then 0.42 g of titanium dioxide are homogeneously suspended in this solution. 14 g of carbomer 971 are sprinkled onto the ethanolic solution on a stirrer set to 300 rpm and 150° C. The system is then sealed and homogenized at room temperature for 60 minutes in a high-speed mixer. Slow stirring is then performed to remove the air that has worked itself into the solution. 1.4 g of strawberry flavoring (e.g., Dragoco) and 238.185 g of an aqueous plant extract from a dry extract of Sambucus nigra, Santella asiatica, Echinacea purpurea (9:0.8:0.2 wt., dry residue content 5.3%) are added. The solution is stirred, and a homogeneous, bubble-free and lump-free, brown gel is obtained, which is spread out on polyester (Hoechst, Hostaphan RN 100) with a wet layer thickness of 2,000 µm. The layer is dried for 30 minutes while the temperature is increased from 40° C. to 60° C.

The backing layer is produced as follows: 18 g of ethyl cellulose are sprinkled onto 153 g of 96% ethanol, and the mixture is stirred at 700 rpm until the ethyl cellulose dissolves. 0.36 g of dye E172 red are dissolved in 2 mL of water. 0.45 g of titanium dioxide are ground in 9 g of castor oil, and 0.0.45 g are added while stirring. The whole mixture is stirred at 300 rpm until a homogeneous, light red, turbid, highly fluid suspension is obtained. The suspension is used to cover the adhesive layer with a wet layer thickness of 1,000 µm, which is likewise dried for 30 minutes while the temperature is increased from 40° C. to 60° C. Mucoadhesive patches with an area of 1.25 cm$^2$ and an elliptical shape are then punched out of the sheet. The patches each contain 4.5 mg of dry extract and are intended for the treatment of gingivitis and periodontitis. These patches are packaged in a pouch of composite packaging material. When they are removed from the pouch or applied to the mucous membrane, they delaminate between the adhesive layer and the backing layer.

To Illustrate the In Vitro Release of Example 1:

To illustrate that binding does not occur in the active substance layer when the proper ratio of anionic and cationic polymers is present, the in vitro release was compared. The release occurred in a blade agitator according to EP in 200 mL of phosphate buffer at 50 rpm and 37° C., such that the patches are fixed with their backing layers on the adhesive tape of the disk. The samples were analyzed by HPLC (temp. 40° C., column: Interchrom (Interchim) Uptisphere UP5TF$15QS, 150 mm×3.0 mm. Eluent A: 6.8 g±0.05 g of monobasic potassium phosphate are dissolved in 1,000 mL of water, and the pH is adjusted to 4.6 with 5 M KOH. Eluent B: 100 mL of Milli-Q water+400 mL of acetonitrile+500 mL of methanol are thoroughly mixed and irradiated with ultrasound for at least 10 minutes; gradient: 25% eluent B, linearly increasing to 60% eluent B from 0 to 15 minutes, starting at 15 minutes decreasing to 25% eluent B again; detection isoquercetrin 20 µL, stop at 15 minutes).

All values in mg/1.25 cm$^2$; mean value of 6 samples:

| Time, h | Example 1 |
|---------|-----------|
| 0 | 0 |
| 1 | 0.041 mg isoquercitrin = 91% |

As the table shows, the release is nearly complete after 1 hour with the example in accordance with the invention. Also, despite the small amounts of the quantified marker substance isoquercetin (isoquercitrin), it can be analytically well characterized.

The following were determined as quality-determining parameters:

Weight per Surface Area: determined as the mean value of 20 patches per weighing, value given in mg/cm$^{-1}$.

Loss upon Drying: determined with 3 patches according to European Pharmacopoeia 2.2.32, vacuum-dried in the desiccator at room temperature for 24 hours, mean value in %.

Adhesive Strength: determined in vitro with 3 patches, hydrated for 2 h at 70%, Frank apparatus, "Peel", steel plate, value given in N.

Release In Vitro: European Pharmacopoeia 2.9.4, as described above.

Content: n=10 for uniformity; analyzed by extraction for 4 h on a circular shaker at room temperature in 20 mL of phosphate buffer by HPC against an external standard, as described for the release determination. The content of 45 μg per patch of the marker substance isoquercetin was used.

The invention claimed is:

1. A patch for the administration of active substances to body orifices or body parts with a mucosal lining of the epidermis, which consists of an adhesive layer and a backing layer, with the backing layer containing a matrix of a nonionic and an anionic hydrocolloid in a weight ratio of 2:1 to 5:1, and with the adhesive layer containing a nonionic and an anionic hydrocolloid in the opposite weight ratio of 1:2 to 1:5.

2. A patch in accordance with claim 1, wherein the backing layer is a matrix of a nonionic and an anionic hydrocolloid in a ratio of 3:1, while the adhesive layer is a matrix of a nonionic and an anionic hydrocolloid in the opposite ratio of 1:3.

3. A patch in accordance with claim 1, wherein the nonionic hydrocolloid is a hydroxypropylmethyl cellulose or ethyl cellulose.

4. A patch in accordance with claim 1, wherein the nonionic hydrocolloid is selected from the group consisting of guar gum, carob bean flour, polyvinyl pyrrolidone, and starch.

5. A patch in accordance with claim 1, wherein the anionic hydrocolloid is carbomer (polyacrylic acid) or gum arabic (salt of arabic acid).

6. A patch in accordance with claim 1, wherein the anionic hydrocolloid is selected from the group consisting of agar, alginic acid, carboxymethyl cellulose, carrageenin, gelatin type B, karaya gum, pectin, tragacanth, and polymethylvinyl ether/maleic anhydride.

7. A patch in accordance with claim 1, wherein the weight ratio of the nonionic and anionic hydrocolloids in the total patch is 1:1 to 1:5.

8. A patch in accordance with claim 1, wherein the weight ratio of the nonionic and anionic hydrocolloids in the total patch is 1:1 to 1:2.

9. A patch in accordance with claim 1, wherein the adhesive layer and the backing layer are inseparably joined, which is accomplished by means of the aforementioned proportions of the nonionic and anionic polymers.

10. A patch in accordance with claim 1, wherein the active substances are selected from the group consisting of antiseptics, antimycotics, virostatics, antibiotics, local anesthetics, corticoids, and vitamins.

11. A patch in accordance with claim 1, wherein the active substances are aqueous and/or alcoholic extracts of plants selected from the group consisting of Echinacea, Sambucus, Matricaria, Thymus, Camiphora, Salix, Camelia, Salvia, Melissa, Myrtillum; and Allium.

12. A patch in accordance with claim 1, wherein flavorings, sweeteners, coloring agents, stabilizers, antioxidants, preservatives, surface-active substances; or fillers are added both in the adhesive layer and the backing layer.

* * * * *